US00PP10888P

United States Patent [19]

Bradford et al.

[11] Patent Number: Plant 10,88

[45] Date of Patent: May 11, 199

[54] NECTARINE TREE NAMED 'WESTERN PRIDE'

[76] Inventors: Lowell Glen Bradford, 12439 E. Savana Rd.; Norman G. Bradford, 11875 E. Savana Rd, both of Le Grand, Calif. 95333

[21] Appl. No.: 08/975,099

[22] Filed: Nov. 20, 1997

[51] Int. Cl.[6] ..... A01H 5/00

[52] U.S. Cl. ..... Plt./192

[58] Field of Search ..... Plt./40.1, 41.3, Plt./192, 187, 198

[56] References Cited

U.S. PATENT DOCUMENTS

P.P. 6,363 11/1988 Bradford et al. ..... Plt./41

P.P. 7,049 10/1989 Bradford et al. ..... Plt./4

*Primary Examiner*—Howard J. Locker
*Assistant Examiner*—Ashwin Mehta

[57] ABSTRACT

The present invention relates to a nectarine tree, *Prunu persica*, and more particularly to a new and distinct variet broadly characterized by a large size, vigorous, self-fertile productive and regular bearing tree. The fruit matures unde the ecological conditions described in mid July, with firs picking on Jul.13,1997. The fruit is uniformly large in size acidic and sweet in flavor, globose in shape, freegstone in type, firm in texture, and mostly red in skin color. The variety was a first generation cross using an unnamed freestone peach as the selected seed parent and 'August Red' (U.S. Plant Pat. No. 6,363) nectarine as the selected pollen parent.

1 Drawing Sheet

1

BACKGROUND OF THE VARIETY

In a continuing effort to improve the quality of fresh market and shipping fruits, we, the inventors, typically hybridize a large number of nectarine and peach seedlings each year. The present invention relates to a new and distinct variety of nectarine tree, which has been denominated varietally as 'Western Pride'. The present variety was developed by us in 1987 in a cultivated area of our experimental orchard at Bradford Farms near Le Grand, Calif. in Merced County (San Joaquin Valley). It was a first generation cross using an unnamed freestone peach as the selected seed parent and 'August Red' (U.S. Plant Pat. No. 6,363) nectarine as the selected pollen parent. Subsequent to origination of the present variety of nectarine tree, we asexually reproduced it by budding and grafting, and such reproduction of plant and fruit characteristics were true to the original plant in all respects. The reproduction of the variety included the use of Nemaguard Rootstock, the standard of the stone fruit industry in central California, upon which the present variety was compatible and true to type.

The present variety is most similar to the 'Summer Bright' nectarine, (U.S. Plant Pat. No. 7,049), by producing yellow flesh nectarines that mature in the latter part of July, that have sweet acidic flavor, and that are mostly red in skin color, but is distinguished therefrom and an improvement thereon by requiring higher chilling, by blooming later, and by producing fruit that matures about 5 days later, is larger in size, and is freestone instead of clingstone.

The present variety is similar to its pollen parent, 'August Red' (U.S. Plant Pat. No. 6,363) by producing large yellow flesh nectarines that are mostly red in skin color, but is distinguished therefrom by producing fruit that ripens about about month earlier and that is freestone instead of clingstone.

DRAWING

The accompanying photograph exhibits four whole fruits positioned to display the characteristics of the skin color and form, one fruit divided around the suture plane to reveal the flesh and stone, and typical leaves.

2

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm eating ripe on Jul. 16, 1997. All major color code designations are by reference to the Inter-Society Color Council, National Bureau of Standards. Common color names are also used occasionally.

Tree

Size: Large, reaching a height of 12' [3.66 meters] on a 4th leaf graft on Nemaguard rootstock utilizing typical dorman pruning.

Vigor: Vigorous, responding typically to irrigation and fertilization.

Growth: Upright and dense.

Form: Vase formed.

Hardiness: Hardy, able to survive typical central California winters.

Fertility: Self-fertile.

Production: Very productive, thinning necessary.

Bearing: Regular bearer, with no alternate bearing yet observed.

Trunk:

*Size.*—Medium, reaching a diameter of 4" [101.6 mm.] after the 4th growing season on Nemaguard rootstock.

*Texture.*—Medium rough, with roughness increasing with age.

*Bark color.* —Grayish brown [61. gy.Br].

*Lenticels.*—Numerous. Color: Dark orange yellow [72. d.OY]. Average size: ⅛" to ⅛" [3.2–9.5 mm.].

Branches:

*Size.*—Medium, typical of the species.

*Texture.*—Smooth on 1st year wood, increasing roughness with age.

*Color.*—1st year wood topside: Dark pink [6. d.Pk]. 1st year wood underside: Moderate yellow green [120. m.YG]. Older wood: Moderate brown [58. m.Br].

*Lenticels.*—Numerous, small, color; Dark orange yellow [72. d.OY]. Average size: 1/16" [1.6 mm.].

eaves:

*Size:*—Medium. Average length: 6" [152.4 mm.]. Average width: 1½" [38.1 mm.].

*Thickness.*—Medium.

*Form.*—Elliptical.

*Apex.*—Acuminaate.

*Base.*—Acute.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Petiole.*—Average length: ½" [12.7 mm.]. Average thickness: 1/16" [1.6 mm.]. Color: Brilliant yellow green [116. brill.YG].

*Stipules.*—Numerous, 2 per leaf, up to 6 per growing tip. Average length: ⅜" [9.5 mm.].

*Glands.*—Numbers: 2 to 4 per leaf. Position: Oppositely positioned on petiole and base of blade. Size: Medium. Form: Reniform. Color: Brilliant yellow green [116. brill.YG].

Flower buds:

*Hardiness.*—Hardy, with respect to central California winters.

*Chilling requirement.*—Approximately 850 hours below 45° F. [7° C.] during the dormant season.

*Diameter.*—Typically 5/16" [7.9 mm.] 1 week before bloom.

*Length.*—Typically ½" [12.7 mm.] 1 week before bloom.

*Form.*—Free.

*Surface.*—Pubescent.

Flowers:

*Blooming period.*—Late as compared with other varieties.

*Onset of bloom.*—One percent on Mar. 4, 1997.

*Fragrance.*—Slight to moderate.

*Type.*—Non-showy.

*Average diameter.*—1 ⅜" [34.9 mm].

*Color.*—Dark purplish pink [251. d.pPk].

Fruit

Maturity when described: Firm eating ripe, Jul. 16, 1997.

Date of first picking: Jul. 13, 1997.

Date of last picking: Jul. 25, 1997.

Size: Uniform, large.

*Average diameter axially.*— 2⅞" [73.0 mm.].

*Average transversely in suture plane.*— 2 ⅞" [73.0 mm.].

*Typical weight.*—7.25 ounces [206 grams].

Form: Globose, uniform, symmetrical.

*Longitudinal section form.*—Round.

*Transverse section through diameter.*—Round.

Suture: A shallow groove extending from the base to slightly beyond the apex with a slight depression beyond the pistil point.

Ventral surface: Rounded, lipped toward the apex.

Lips: Slightly unequal.

Cavity: Flaring, circular, suture showing on one side, stem marks typical. *Depth.*—7/16" [11.1 mm.]. *Breadth.*— 1 1/16" [27.0 mm.].

Base: Rounded to somewhat truncate.

Apex: Rounded.

Pistil point: Negligible in length, oblique and depressed within the suture.

Stem: Medium.

*Average length.*—⅜" [9.5 mm.].

*Average width.*—3/16" [4.8 mm.].

Skin:

*Thickness.*—Medium.

*Texture.*—Medium.

*Tenacity.*—Tenacious to flesh.

*Tendency to crack.*—None observed.

*Color.*—Strong red orange [35. s.rO] blending into a brilliant orange yellow [67. brill.OY] background.

Flesh:

*Color.*—Brilliant yellow [83. brill.Y] with slight moderate red [15. m.R] streaking.

*Surface of pit cavity.*—Moderate red [15. m.R] fibers.

*Amygdalin.*—Moderate.

*Juice.*—Moderate, rich.

*Texture.*—Firm, crisp.

*Fibers.*—Abundant, fine.

*Ripens.*—Evenly.

*Flavor.*—Acidic and sweet, with 15 brix.

*Aroma.*—Slight.

*Eating quality.*—Very good.

Stone

Type: Freestone.

Form: Oval

Base: Straight.

Apex: Acute.

Sides: Equal.

Surface: Irregularly furrowed toward the apex and pitted toward the base.

Ridges: Jagged toward the base.

Color: Dark yellowish brown [78. d.yBr].

Pit wall: 5/16" [7.9 mm.] thick.

Tendency to split: Slight.

Kernel:

*Form.*—Oval.

*Taste.*—Sweet.

*Viable.*—Yes.

*Average width.*—9/16" [14.3 mm.].

*Average length.*—13/16" [20.6 mm.].

*Skin color.*—Pale yellow [89. p.Y] with light grayish brown [60. 1.gy.Br] veins.

*Pellicle color.*—Light grayish brown [60. 1.gy.Br].

*Amygdalin.*—Scant.

Use

Market: Fresh and long distance shipping.

Keeping quality: Fruit quality observed to remain in good condition in excess of 17 days in cold room at 36° Fahrenheit [2° Celsius].

Resistance to insects: No unusual susceptibilities noted.

Resistance to diseases: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, that is most similar to the 'Summer Bright' nectarine, (U.S. Plant Pat. No. 7,049), by producing yellow flesh nectarines that mature in the latter part of July, that have sweet acidic flavor, and that are mostly red in skin color, but is distinguished therefrom and an improvement thereon by requiring higher chilling, by blooming later, and by producing fruit that matures about days later, is larger in size, and is freestone instead c clingstone.

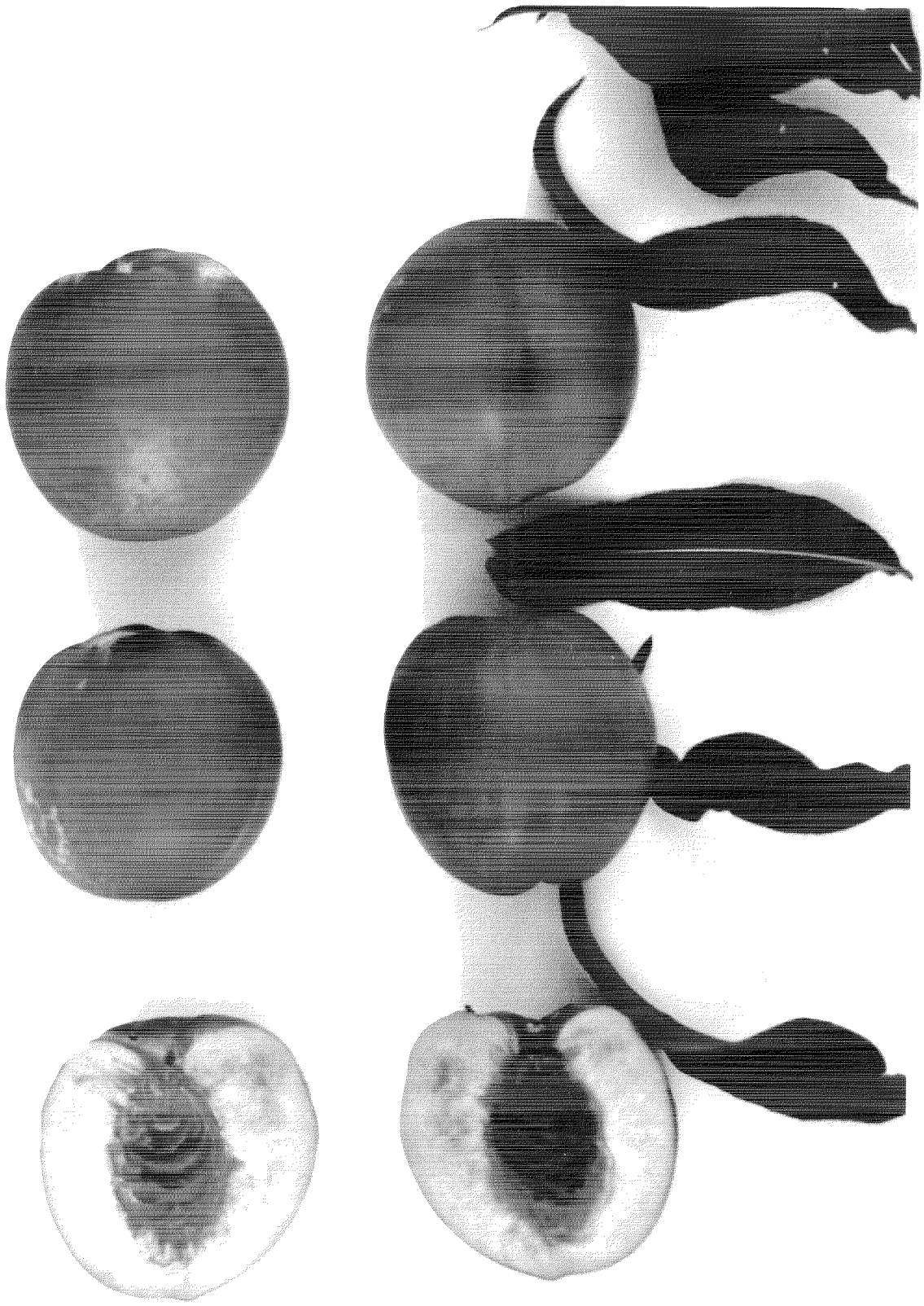

* * * * *